United States Patent [19]

Hirakawa et al.

[11] Patent Number: 5,614,220
[45] Date of Patent: Mar. 25, 1997

[54] PHARMACEUTICAL PREPARATION CONTROLLED TO RELEASE MEDICINAL ACTIVE INGREDIENT AT TARGETED SITE IN INTESTINAL TRACT

[75] Inventors: Yoshiyuki Hirakawa, Kobe; Hiroyuki Yoshino, Suita; Katsuji Uemura, Amagasaki; Eiji Fukui, Kakogawa; Tami Hanamori, Kobe, all of Japan

[73] Assignee: Tanabe Seiyaku Co., Ltd., Osaka, Japan

[21] Appl. No.: 385,982

[22] Filed: Feb. 9, 1995

[30] Foreign Application Priority Data

Feb. 10, 1994 [JP] Japan .................. 6-016028

[51] Int. Cl.[6] ........................... A61K 9/36
[52] U.S. Cl. .................. 424/480; 424/482; 424/469; 424/461
[58] Field of Search .................. 424/480, 482, 424/469, 461

[56] References Cited

U.S. PATENT DOCUMENTS

| | | | |
|---|---|---|---|
| 4,853,230 | 8/1989 | Lovgren et al. | 424/466 |
| 5,068,110 | 11/1991 | Fawzi | 424/461 |
| 5,167,964 | 12/1992 | Muhammad et al. | 424/482 |
| 5,378,474 | 1/1995 | Morella et al. | 424/469 |

FOREIGN PATENT DOCUMENTS

| | | |
|---|---|---|
| 2683146 | 10/1992 | France . |
| 2262445 | 10/1992 | United Kingdom . |
| 9004386 | 5/1990 | WIPO . |

OTHER PUBLICATIONS

Journal of Controlled Release, 2 (1985), PP27–38.
Chem. Pharm. Bull., 40(11), pp. 3036–3041 (1992).
Annals of the New York Academy of Sciences, vol. 618, pp.428–440.
Science, vol. 233, pp.1081–1084 (1986).
20th International Symposium on Controlled Release of Bioactive Material, pp.318–319 (Jun. 1993).

Primary Examiner—Thurman K. Page
Assistant Examiner—William E. Benston, Jr.
Attorney, Agent, or Firm—Birch, Stewart, Kolasch & Birch, LLP

[57] ABSTRACT

A pharmaceutical preparation for oral administration comprising
(a) a core containing a medicinal active ingredient,
(b) a press-coated layer comprising a pH-independently water-soluble polymer, said layer being provided around the core and
(c) a film comprising an enteric polymer, said film being provided around the press-coated layer. In the pharmaceutical preparation of the present invention, the medicinal active ingredient is not released during residence in the stomach and, after forwarded from the stomach, until reaching a targeted site in the intestine, and thereafter is quickly released, so that the medicinal active ingredient is efficiently delivered to the targeted site in the intestinal tract.

4 Claims, 3 Drawing Sheets

| PHARMACEUTICAL PREPARATION | AMOUNT OF PRESS-COATED LAYER |
|---|---|
| A | 200 mg / tablet |
| B | 160 mg / tablet |
| C | 140 mg / tablet | ism of Science, 618, 428–440 (1991)), a pharmaceutical preparation obtained by utilizing a technique for controlling the starting time of the release (Chemical & Pharmaceutical Bulletin. 3036–3041 (1992)) and the like, as well as pharmaceutical preparations obtained by using known techniques such as an enteric pharmaceutical preparation and a sustained release pharmaceutical preparation.

PHARMACEUTICAL PREPARATION CONTROLLED TO RELEASE MEDICINAL ACTIVE INGREDIENT AT TARGETED SITE IN INTESTINAL TRACT

BACKGROUND OF THE INVENTION

The present invention relates to a pharmaceutical preparation controlled to release a medicinal active ingredient at a targeted site the gastrointestinal tract, and more particularly to a pharmaceutical preparation for oral administration from which a medicinal active ingredient can be selectively delivered to any specific site in the intestinal tract.

Selective delivery of a medicinal active ingredient to a specific site in the intestinal tract has been desired in drug therapies, for instance, a local therapy for inflammatory disease in the intestinal tract such as ulcerative colitis or Crohn's disease, or an oral administrative therapy with a medicinal compound of a peptide which is apt to be decomposed chemically or enzymatically in the intestinal tract, with a medicinal compound of which the absorption site is limited, or with other medicinal compound.

In order to efficiently realize the selective delivery of a medicinal active ingredient to a specific site in the intestinal tract, it is necessary to design a pharmaceutical preparation taking into account the physical and physiological environment in the human gastrointestinal tract and the traveling time of the pharmaceutical preparation in the intestinal tract. With respect to the physical and physiological environment in the gastrointestinal tract, it is recognized that the value of pH in the stomach is usually 1.8 to 4.5 in a healthy human and that the value of pH in the intestines is 6.5 to 7.5 and the pH does not essentially differ between the small intestine and the large intestine. According to the results of the widespread research of Davis et al., the residence time of a pharmaceutical preparation in the human stomach is 0.5 to 10 hours and further not only the inter-individual variation thereof is large, but also the residence time is considerably influenced, for example, by feeding, a size of the pharmaceutical preparation to be administered and the like. However, the traveling time of a pharmaceutical preparation through the small intestine is generally recognized to be 3±1 hours and the inter- and intra-individual variation is relatively small (Journal of Controlled Release, 2, 27–38 (1985)).

With respect to a method by which a medicinal active ingredient can be selectively delivered to a specific site in the intestinal tract, hitherto various researches have been done. There have been proposed a pharmaceutical preparation wherein a sustained release pharmaceutical preparation is coated with an enteric coating (Annals of the New York Academy of Science, 618, 428–440 (1991)), a pharmaceutical preparation obtained by utilizing a technique for controlling the starting time of the release (Chemical & Pharmaceutical Bulletin. 3036–3041 (1992)) and the like, as well as pharmaceutical preparations obtained by using known techniques such as an enteric pharmaceutical preparation and a sustained release pharmaceutical preparation.

However, every conventional method has a problem such as insufficient site-selectivity or poor practicality due to peculiarity of the material to be used. For example, in case of using the enteric pharmaceutical preparation, the release of a medicinal active ingredient starts abruptly at the upper small intestine resulting in consumption of almost of the medicinal active ingredient by absorption or decomposition before the medicinal active ingredient reaches the targeted site in the intestine, although the release of the medicinal active ingredient can be effectively suppressed in the stomach. In case using the sustained release pharmaceutical preparation, a considerable amount of a medicinal active ingredient is released when the pharmaceutical preparation stays in the stomach and passes through the small intestine because the medicinal active ingredient is continuously released.

Further, in order to release a medicinal active ingredient at the large intestine, there has been recently developed a system utilizing the ecosystem of specific microorganisms in the large intestine. For example, in a pharmaceutical preparation wherein a composition containing a medicinal active ingredient is coated with a novel polymer having an azo group, or the composition containing a medicinal active ingredient is dispersed in the new polymer having an azo group to form a matrix type of pharmaceutical preparation (Science, 233, 1081–1084 (1986)), the polymer is decomposed in the large intestine by enterobacteria having azoreductase activity and the medicinal active ingredient is thereby released at the large intestine. However, for practical use, there are still many problems to be solved, for example, regarding the safety of the polymer itself, the controllability of the decomposition rate thereof, and the like.

An object of the present invention is to solve the above-mentioned problems the conventional pharmaceutical preparations, and provide a pharmaceutical preparation for oral administration by which a medicinal active ingredient can be effectively released at a targeted site in the intestinal tract.

This and the other objects of the present invention will become apparent from the description hereinafter.

SUMMARY OF THE INVENTION

In accordance with the present invention, there is provided a pharmaceutical preparation for oral administration comprising (a) a core containing a medicinal active ingredient, (b) a press-coated layer comprising a PH-independently water-soluble polymer, said layer being provided around the core and (c) a film comprising an enteric polymer, said film being provided around the press-coated layer.

The pharmaceutical preparation of the present invention has the following characteristics: when the pharmaceutical preparation is orally administered, the release of a medicinal active ingredient does not occur at all during residence of the pharmaceutical preparation in the stomach and, after discharge from the stomach, until the preparation reaches a desirable targeted site in the intestine and thereafter, the release of the ingredient starts rapidly. In case of using a medicinal active ingredient as a drug required to be selectively delivered to a specific site in the intestinal tract, an excellent pharmaceutical preparation having high availability can be provided.

DETAILED DESCRIPTION OF THE INVENTION

Figure 1:
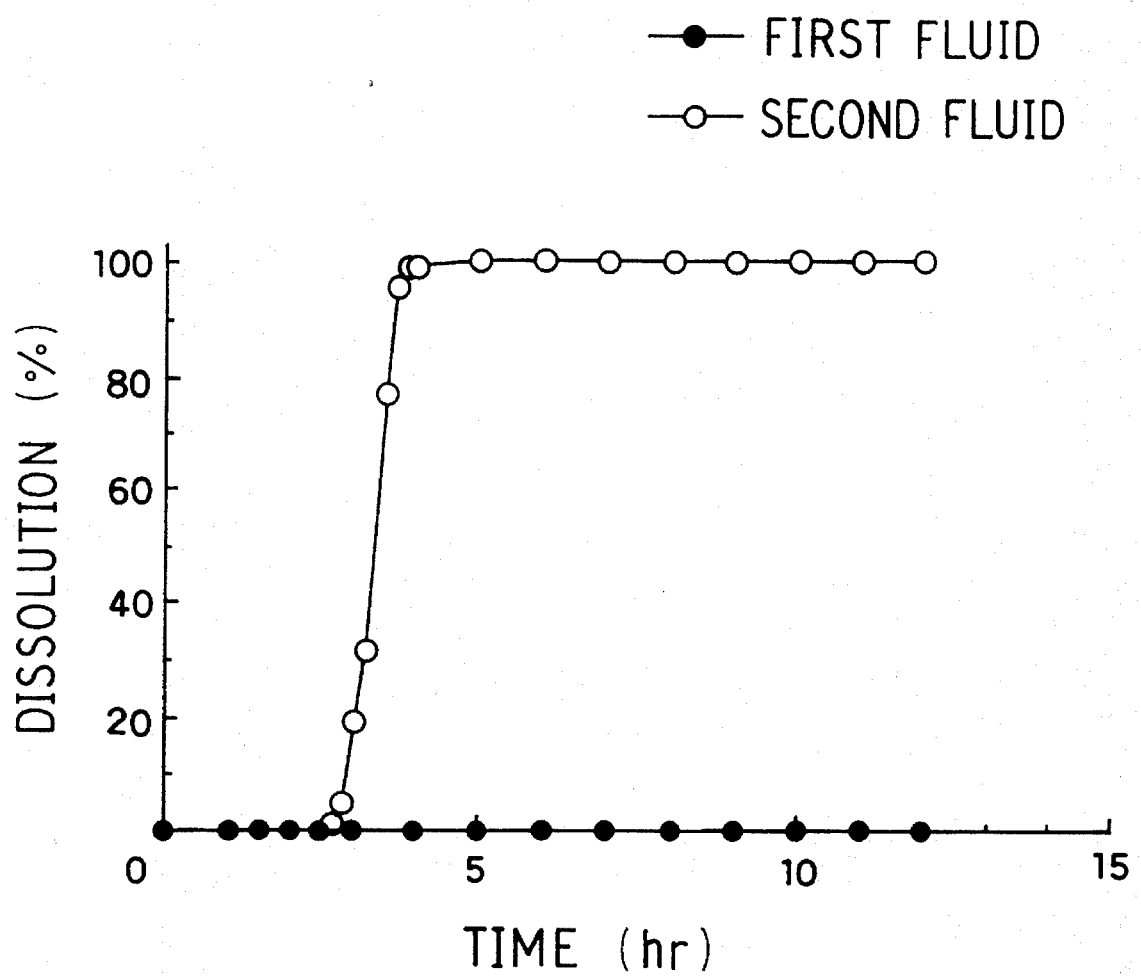
FIG. 1 is a graph showing the result of the dissolution test with the first fluid and the second fluid of the dissolution test in Japanese Pharmacopoeia XII (hereinafter referred to as JPXII) using a pharmaceutical preparation in Example 1.

The present invention provides a pharmaceutical preparation from which a medicinal active ingredient can be selectively released at a targeted site in the intestinal tract, by combining an enteric polymer, which dissolves dependent on a value of pH, and a press-coated layer comprising a pH-independently water-soluble polymer. In the pharmaceutical preparation of the present invention, the concrete structure thereof can be suitably selected so that a medicinal active ingredient can be released at the desirable targeted site in the intestinal tract.

In the pharmaceutical preparation of the present invention, the functions of the film (c) comprising an enteric polymer are to prevent the penetration of water during residence of the pharmaceutical preparation in the stomach so that the contents [core (a) and press-coated layer (b)] thereof can be protected, and to quickly dissolve according as the surrounding pH increases after discharge of the pharmaceutical preparation from the stomach so that the contents are forwarded to the upper small intestine. The press-coated layer (b) perfectly prevents the penetration of water into the core (a), unless the press-coated layer (b) dissolves, and therefore the press-coated layer (b) dissolves, and therefore the press-coated layer (b) suppresses the release of the medicinal active ingredient in the intestine after discharge of the pharmaceutical preparation from the stomach. Namely, the press-coated layer (b) is capable of suppressing the release of the medicinal active ingredient in the intestine until the pharmaceutical preparation reaches near the desirable targeted site.

In order to sufficiently exhibit the above-mentioned capacity in the pharmaceutical preparation of the present invention, it is desirable to determine the coating amount of the film (c) so that the pharmaceutical preparation has sufficient acid resistance and the film (c) prevents the penetration of water into the pharmaceutical preparation during residence in the stomach. It is also desirable to determine the time required for dissolution of the press-coated layer (b) in the intestine so that the press-coated layer (b) can substantially suppress the release of the medicinal active ingredient until the pharmaceutical preparation reaches near the desirable targeted site in the intestine.

From the above-mentioned viewpoints, it desirable that the coating amount of the film (c) is usually determined so that the film (c) prevents the penetration of water during residence in the stomach for a period of about 10 hours which is recognized as the maximum residence time of a pharmaceutical preparation in the stomach, and that in case of targeting the upper large intestine, the coating amount of the press-coated layer (b) is determined so that the press-coated layer (b) can suppress the release of a medicinal active ingredient in the intestines for about 3±1 hours which is recognized as a general traveling time of a pharmaceutical preparation through the small intestine.

The pharmaceutical preparation of the present invention can be suitably designed so that when a dissolution test is carried out according to the dissolution test (puddle method; 37° C.; 100 rpm; 900 ml of dissolution fluid) of JPXII (refer to Example 1), release of a medicinal active ingredient is substantially suppressed for at least 10 hours in the first fluid (pH 1.2), and the release of the medicinal active ingredient is substantially suppressed for at least about 2 hours in the second fluid (pH 6.8) and thereafter the release of the medicinal active ingredient starts quickly. The time required to start the release of the medicinal active ingredient (hereinafter referred to as "lag-time") in the second fluid is set to meet the desired target-site in the intestinal tract. For example, in case that the pharmaceutical preparation of the present invention is designed to have the lag-time of about 2 hours, about 4 hours or about 7 hours, there can be obtained a pharmaceutical preparation wherein release of a medicinal active ingredient is intended to occur at the lower ileum, the ascending colon or the transverse colon. If the pharmaceutical preparation of the present invention is designed to have the lag-time being longer than about 7 hours, there can be obtained a pharmaceutical preparation wherein release of a medicinal active ingredient is intended to occur at the lower large intestine such as the descending colon or the sigmoid colon.

The medicinal active ingredient to be included in the above-mentioned core (a) in the present invention is not particularly limited as long as it is orally administerable. Concrete examples of such medicinal active intredient include chemotherapeutic agents, antibiotics, respiratory stimulants, antitussives, expectorants, antimalignanttumor agents, autonomic agents, psychotropic agents, local anesthetics, muscle relaxants, agents affecting digestive organs, antihistamines, toxicopetic agents, hypnotics, sedatives, antiepileptics, antipyretics, analgesics, antiinflammatory agents, cardiotonics, antiarrhythmic agents, diuretics, vasodilators, antilipemic agents, nutrients, tonics, alteratives, anticoagulants, agents for liver disease, hypoglycemics, antihypertensives and the like.

The amount of the medicinal active ingredient to be included in the core (a) may be determined to be about 0.2 to about 100 w/w %, preferably 0.5 to 50 w/w %, based on a weight of the core (a).

As the pH-independently water-soluble polymer used for the press-coated layer (b), any film-formable polymer usually used in this field which is soluble in an aqueous medium without being influenced by a pH of the aqueous medium can be used. In the present invention, the pH-independently water-soluble polymer may be used alone or in admixture thereof. If necessary, the pH-independently water-soluble polymer may be used in admixture with a water-insoluble polymer, such as ethylcellulose.

Examples of the pH-independently water-soluble polymer include a cellulose derivative such as hydroxypropylcellulose, hydroxypropylmethylcellulose, methylcellulose, hydroxyethylcellulose or methylhydroxyethylcellulose, a synthetic polymer such as polyvinylpyrrolidone, a polysaccharide such as pullulan, a natural high molecular substance such as arabic gum, and the like.

Among the above-mentioned examples, a cellulose derivative such as hydroxypropylcellulose, hydroxypropylmethylcellulose, methylcellulose or hydroxyethylcellulose, and pullulan are preferable. Hydroxypropylcellulose and hydroxypropylmethylcellulose are more preferable, and hydroxypropylcellulose is particularly preferable.

Some kinds of the above-mentioned pH-independently water-soluble polymers have a different polymerization degree. The viscosity of the polymer is different depending on a polymerization degree of the substance. In the present invention, the pH-independently water-soluble polymer having any viscosity, i.e. polymerization degree, can be used alone or in admixture of at least two polymers having different viscosities from each other.

For example, in case of using a hydroxypropylcellulose as the pH-independently water-soluble polymer, two kinds of hydroxypropylcelluloses having a viscosity of 6 to 10 cps and a viscosity of 150 to 400 cps, respectively, as measured in a 2 % aqueous solution at 20° C. may be used alone or in admixture thereof. An example of the hydroxypropylcellulose having a viscosity of 6 to 10 cps as measured in a 2 % aqueous solution at 20° C., is HPC-L (trade name, available from Nippon Soda Co., Ltd.). An example of the hydroxypropylcellulose having a viscosity of 150 to 400 cps as measured in a 2 % aqueous solution at 20° C., is HPC-M (trade name, available from Nippon Soda Co., Ltd.). A hydroxypropylcellulose having the above-mentioned viscosity can be suitably used in admixture thereof by determining the mixing ratio to be about 9:1 to about 1:9 by weight.

As an enteric polymer used for the film (c), any filmformable polymer soluble in an aqueous medium of a pH of not less than 5 and insoluble in an aqueous medium of a pH of less than 5 can be used in the pharmaceutical preparation of the present invention. Examples of such polymer include a cellulose derivative, a polyvinyl derivative, a maleic acid-vinyl compound copolymer, an acrylic copolymer and the like.

Concrete examples of the cellulose derivative include carboxymethylethylcellulose, cellulose acetate phthalate, cellulose acetate succinate, methylcellulose phthalate, hydroxymethylethylcellulose phthalate, hydroxypropylmethylcellulose phthalate, hydroxypropylmethylcellulose acetate succinate and the like. Concrete examples of the polyvinyl derivative include polyvinyl alcohol phthalate, polyvinyl butylate phthalate, polyvinyl acetoacetal phthalate and the like. Concrete examples of the maleic acid-vinyl compound copolymer include poly(vinyl acetate, maleic acid anhydride), poly(vinyl butyl ether, maleic acid anhydride), poly(styrene, maleic acid monoester), and the like. Concrete examples of the acrylic copolymer include poly(methyl acrylate, methacrylic acid), poly(styrene, acrylic acid), poly(methyl acrylate, methacrylic acid, octyl acrylate), poly(methacrylic acid, methyl methacrylate) (e.g. Eudragit L and Eudragit S, each being trade name, available from Röhm Pharma, Germany), and the like.

Among these examples, carboxymethylethylcellulose, hydroxypropylmethylcellulose phthalate, hydroxypropylmethylcellulose acetate succinate, poly(methacrylic acid, methyl methacrylate) and the like are preferably used as the enteric polymer, and particularly carboxymethylethylcellulose, hydroxypropylmethylcellulose phthalate and hydroxypropylmethylcellulose acetate succinate are preferable. The above-mentioned enteric polymer can be used alone or in admixture thereof.

Additionally, in the above-mentioned core (a), the presscoated layer (b) and the film (c) of the pharmaceutical preparation of the present invention, various additives such as an excipient, a binder, a disintegrant, a lubricant and an aggregation-preventing agent which are generally used in this field may be included, if desired.

Concrete examples of the excipient include saccharide such as sucrose, lactose, mannitol or glucose, starch, crystalline cellulose, calcium phosphate, calcium sulfate and the like. Concrete examples of the binder include polyvinylalcohol, polyacrylic acid, polymethacrylic acid, polyvinylpyrrolidone, glucose, sucrose, lactose, realrose, dextrin, sorbitol, mannitol, hydroxyethylcellulose, hydroxypropylmethylcellulose, hydroxypropylcellulose, a polyethyleneglycol, arabic gum, gelatin, agar, starch and the like. Concrete examples of the disintegrant include calcium carboxymethylcellulose, sodium carboxymethylstarch, corn starch, hydroxypropylstarch, partially pregelatinized starch, low-substituted hydroxypropylcellulose, polyvinylpyrrolidone, calcuim cross-linked carboxymethylcellulose and the like. Concrete examples of the lubricant and the aggregation-preventing agent are, for example, talc, magnesium stearate, calcium stearate, colloidal silicon dioxide, stearic acid, a wax, a hydrogenated oil, a polyethyleneglycol, sodium benzoate and the like.

The lag-time, the time required until the release of the medicinal active ingredient starts in the intestine or in the second fluid (pH 6.8) described in JPXII, can be controlled by varying the press-coated layer (b) as below. For example, if the amount of the press-coated layer (b) is increased (or decreased), the lag-time can be prolonged (or reduced). In case that the coating amount of the press-coated layer (b) is almost constant, if a pH-independently water-soluble polymer having larger (or smaller) polymerization degree, i.e. viscosity, is used for the press-coated layer (b), the lag-time can be prolonged (or reduced). Moreover, in case that two or more kinds of the pH-independently water-soluble polymer having different viscosities are used in admixture thereof, the lag-time can be also varied according to the mixing ratio. Namely, the lag-time in the pharmaceutical preparation of the present invention can be suitably controlled to be a desired length by employing a proper combination of the coating amount of the press-coated layer (b), the kind and viscosity of the pH-independently water-soluble polymer, the mixing ratio, and the like.

The dosage form of the pharmaceutical preparation of the present invention is preferably a tablet. The size of the pharmaceutical preparation is not particularly limited, however, the diameter thereof is preferably 4 to 16 mm, more preferably 6 to 12 mm.

The form of the core (a) is preferably a tablet. The size of the core (a) is not particularly limited, however, the diameter thereof is preferably 3 to 15 mm, more preferably 5 to 8 mm.

In the pharmaceutical preparation of the present invention, the thickness of the press-coated layer (b) can be selected without any limitation. The thickness of the presscoated layer (b) is usually determined to 0.4 to 3 mm, preferably 0.5 to 1.5 mm. The coating amount of the press-coated layer (b) corresponding to the above-mentioned thickness, varying according to the size of the core (a), is usually about 150 to about 600 w/w %, preferably 200 to 400 w/w % based on a weight of the core (a).

The coating amount of the film (c), varying according to the enteric polymer used, is usually about 5 to about 50 w/w %, preferably 7 to 20 w/w %, based on a total weight of the core (a) and the press-coated layer (b).

The preparation of the core (a) can be carried out according to the usual procedure for the preparation, for example, as described in Lemingtons Pharmaceutical Sciences, 17, (Mack Publishing Company, published in 1985). For example, in case of preparing a tablet as a core, the tablet can be obtained by tabletting a medicinal active ingredient alone, or if necessary, in admixture with other suitable additives such as an excipient, a binder and a lubricant. If necessary, the above-mentioned medicinal active ingredient or mixture is granulated according to a usual method before the tabletting process.

The press-coating to form the press-coated layer (b) around the core (a) is carried out according to a usual method in this field, for instance, a compression molding method such as a press-coating method or a dry coating method, and the like. For example, the press-coated layer can be formed by press-coating the core (a) with a pH-independently water-soluble polymer alone, or if necessary, in admixture with other suitable additives such as an excipient, a binder, a lubricant and a fluidizing agent. If necessary, the above-mentioned polymer or mixture is granulated according to a usual method before the press-coating process. Then, the press-coated layer is provided on the core. The press-coating can be suitably carried out by means of a press-coating machine or a tabletting machine generally used, under the conditions such that the compressing pressure is, for instance, 200 to 1200 kg/cm$^2$ and the compressing rate is 1 to 20 mm/minute.

The coating of the press-coated layer (b) with the film (c) can be carried out according to a process usually used in this field such as a fluidizing coating process, a pan coating process or a tumbling and fluidizing coating process, by means of, for example, a fluidizing coating apparatus, a pan coating apparatus, a tumbling and fluidizing coating and granulating apparatus or the like. Both an aqueous coating method and a non-aqueous coating method generally used in this field can be employed for the above-mentioned coating. In addition, a plasticizer, an aggregation-preventing agent and the like which are usually used can be suitably added to the coating solution. Alternatively, the coating with the film (c) can be carried out by the press-coating process as mentioned above.

The present invention is more specifically described and explained by means of the following Examples and Experimental Examples. It is to be understood that the present invention is not limited to the Examples, and various changes and modifications may be made in the invention without departing from the spirit and scope thereof.

EXAMPLE 1

Diltiazem hydrochloride (300 g) and corn starch (200 g) were mixed together. The mixture was granulated according to a wet granulation method using a binding solution (180 g) of polyvinylpyrrolidone (trade name: Kollidon 30, available from BASF) (90 g) dissolved in ethanol (90 g). The obtained granules were dried and shieved to obtain granules for tabletting (585 g). A part of thus obtained granules for tabletting (530 g), calcium citrate (120 g), calcium carboxymethylcellulose (trade name: ECG-505, available from Gotoku Chemical Co., Ltd.) (40 g) and magnesium stearate (10 g) were mixed together. The mixture was tabletted by means of a rotary tabletting machine (F-9 Type, made by Kikusui Seisakusho Ltd.) to obtain a plain tablet (a core tablet) having a diameter of 6 mm and a weight of 70 mg.

The obtained plain tablet was press-coated with a mixture of powder of hydroxypropylcellulose (trade name: HPC-L, having a viscosity of 6 to 10 cps as measured at 20° C. in a 2 % aqueous solution, available from Nippon Soda Co., Ltd.), and hydroxypropylcellulose (trade name: HPC-M, having a viscosity of 150 to 400 cps as measured at 20° C. in a 2 % aqueous solution, available from Nippon Soda Co., Ltd.) (the mixing ratio, by weight (w/w) (hereinafter referred to as "the mixing ratio") 9:1) in a coating amount of 200 mg per tablet by means of a press-coating machine (Correct 18HUK-DC Type, made by Kikusui Seisakusho Ltd.) to obtain a press-coated tablet having a diameter of 9 mm and a weight of 270 mg.

Then, the obtained press-coated tablet was spray-coated with a 8 w/w % coating solution of hydroxypropylmethylcellulose acetate succinate (trade name: HPMCAS-M, available from The Shin-etsu Chemical Co., Ltd.) and triethyl citrate (the mixing ratio, 10:1) dissolved in 80 w/w % ethanol, in a coating amount of 30 mg per tablet by means of a fluidized bed coating apparatus (MODEL HCT-MINI HICOATER, made by Freund Ind. Co., Ltd.) to obtain a pharmaceutical preparation of the present invention.

With respect to thus obtained pharmaceutical preparation of the present invention, a dissolution test (puddle method) was carried out with the first fluid of the test in JPXII (pH 1.2) and the second fluid of the test in JPXII (pH 6.8) according to the description of the dissolution test in JPXII. The dissolution test was carried out using 900 ml of the dissolution fluid at 37° C. and at the rotation speed of 100 rpm.

The results of the test is shown in FIG. 1. As it is clear from the dissolution pattern of diltiazem hydrochloride being a medicinal active ingredient, in the first fluid, the medicinal active ingredient was not released at all for long time (at least 12 hours), which means that the acid resistance of the pharmaceutical preparation was maintained sufficiently. In the second fluid, the medicinal active ingredient was quickly released after the lag-time of about 3 hours in a pulsatile dissolution pattern.

EXAMPLE 2

The plain tablet containing diltiazem hydrochloride obtained in Example 1 was press-coated with a mixture of powder of hydroxypropylcellulose (trade name: HPC-L, having a viscosity of 6 to 10 cps as measured at 20° C. in a 2 % aqueous solution, available from Nippon Soda Co., Ltd.) and hydroxypropylcellulose (trade name: HPC-M, having a viscosity of 150 to 400 cps as measured at 20° C. in a 2 % aqueous solution, available from Nippon Soda Co., Ltd.) (the mixing ratio, 8:2) in a coating amount of 200 mg per tablet by means of a press-coating machine (Correct 18HUK-DC Type, made by Kikusui Seisakusho Ltd.) to obtain a press-coated tablet having a diameter of 9 mm and a weight of 270 mg.

Then, the obtained press-coated tablet was spray-coated with a 8 w/w % coating solution of hydroxypropylmethylcellulose acetate succinate (trade name: HPMCAS-M, available from The Shin-etsu Chemical Co., Ltd.) and triethyl citrate (the mixing ratio, 10:1) dissolved in 80 w/w % ethanol, in a coating amount of 0 mg per tablet by means of a fluidized bed coating apparatus (MODEL HCT-MINI HICOATER, made by Freund Ind. Co., Ltd.) to obtain a pharmaceutical preparation of the present invention.

With respect to thus obtained pharmaceutical preparation of the present invention, a dissolution test was carried out with the second fluid of the test in JPXII under the same conditions in Example 1. In the second fluid, the medicinal active ingredient was quickly released after the lag-time of about 5 hours.

EXAMPLE 3

The plain tablet containing diltiazem hydrochloride obtained in Example 1 was press-coated with a mixture of powder of hydroxypropylcellulose (trade name: HPC-L, having a viscosity of 6 to 10 cps as measured at 20° C. in a 2 % aqueous solution, available from Nippon Soda Co., Ltd.) and hydroxypropylcellulose (trade name: HPC-M, having a viscosity of 150 to 400 cps as measured at 20° C.

in a 2 % aqueous solution, available from Nippon Soda Co., Ltd.) (the mixing ratio, 6:4) in a coating amount of 200 mg per tablet by means of a press-coating machine (Correct 18HUK-DC Type, made by Kikusui Seisakusho Ltd.) to obtain a press-coated tablet having a diameter of 9 mm and a weight of 270 mg.

Then, the obtained perss-coated tablet was spray-coated with a 8 w/w % coating solution of hydroxypropylmethylcellulose acetate succinate (trade name: HPMCAS-M, available from The Shin-etsu Chemical Co., Ltd.) and triethyl citrate (the mixing ratio, 10:1) dissolved in 80 w/w % ethanol, in a coating amount of 30 mg per tablet by means of a fluidized bed coating apparatus (MODEL HCT-MINI HICOATER, made by Freund Ind. Co., Ltd.) to obtain a pharmaceutical preparation of the present invention.

With respect to thus obtained pharmaceutical preparation of the present invention, a dissolution test was carried out with the second fluid of the test in JPXII under the same conditions in Example 1. In the second fluid, the medicinal active ingredient was quickly released after the lag-time of about 8 hours.

EXAMPLE 4

5-Aminosalicylic acid (300 g) and corn starch (200 g) were mixed together. The mixture was granulated according to a wet granulation method using a binding solution (180 g) of polyvinylpyrrolidone (trade name: Kollidon 30, available from BASF) (90 g) dissolved in ethanol (90 g). The obtained granules were dried and shieved to obtain granules for tabletting (585 g). A part of thus obtained granules for tabletting (530 g), calcium citrate (120 g), calcium carboxymethylcellulose (trade name: EGG-505, available from Gotoku Chemical Co., Ltd.) (40 g) and magnesium stearate (10 g) were mixed together. The mixture was tabletted by means of a rotary tabletting machine (F-9 Type, made by Kikusui Seisakusho Ltd.) to obtain a plain tablet (a core tablet) having a diameter of 6 mm and a weight of 70 mg.

The obtained plain tablet was Dress-coated with a mixture of powder of hydroxypropylcellulose (trade name: HPC-L, having a viscosity of 6 to 10 cps as measured at 20° C. in a 2 % aqueous solution, available from Nippon Soda Co., Ltd.) and hydroxypropylcellulose (trade name: HPC-M, having a viscosity of 150 to 400 cps as measured at 20° C in a 2 % aqueous solution, available from Nippon Soda Co., Ltd.) (the mixing ratio, 9:1) in a coating amount of 200 mg per tablet by means of a press-coating machine (Correct 18 HUK-DC Type, made by Kikusui Seisakusho Ltd.) to obtain a press-coated tablet having a diameter of 9 mm and a weight of 270 mg.

Then, the obtained press-coated tablet was spray-coated with a 8 w/w % coating solution of hydroxypropylmethylcellulose acetate succinate (trade name: HPMCAS-M, available from The Shin-etsu Chemical Co., Ltd.) and triethyl citrate (the mixing ratio, 10:1) dissolved in 80 w/w % ethanol, in a coating amount of 30 mg per tablet by means of a fluidized bed coating apparatus (MODEL HCT-MINI HICOATER, made by Freund Ind. Co., Ltd.) to obtain a pharmaceutical preparation of the present invention.

With respect to thus obtained pharmaceutical 1. 5 preparation of the present invention, a dissolution test was carried out with the second fluid of the test in JPXII under the same conditions in Example 1. In the second fluid, the medicinal active ingredient was quickly released after the lag-time of about 3 hours.

EXAMPLE 5

The plain tablet containing 5-aminosalicylic acid obtained in Example 4 was press-coated with a mixture of powder of hydroxypropylcellulose (trade name: HPC-L, having a viscosity of 6 to 10 cps as measured at 20° C. in a 2 % aqueous solution, available from Nippon Soda Co., Ltd.), hydroxypropylcellulose (trade name: HPC-M, having a viscosity of 150 to 400 cps as measured at 20° C. in a 2 % aqueous solution, available from Nippon Soda Co., Ltd.) and lactose (the mixing ratio, 3:2:2) coating amount of 200 mg per tablet by means of a press-coating machine (Correct 18 HUK-DC Type, made by Kikusui Seisakusho Ltd.) to obtain a press-coated tablet having a diameter of 9 mm and a weight of 270 rag.

Then, the obtained press-coated tablet was spray-coated with a 8 w/w % coating solution of carboxymethylethylcellulose (trade name: CMEC, available from Freund Industrial Co., Ltd.) and triacetin (the mixing ratio, 10:1) dissolved in 80 w/w % ethanol, in a coating amount of 30 mg per tablet by means of a fluidized bed coating apparatus (MODEL HCT-MINI HICOATER, made by Freund Ind. Co., Ltd.) to obtain a pharmaceutical preparation of the present invention.

With respect to thus obtained pharmaceutical preparation of the present invention, a dissolution test was carried out with the second fluid of the test in JPXII under the same conditions in Example 1. In the second fluid, the medicinal active ingredient was quickly released after the lag-time of about 5 hours.

EXAMPLE 6

The plain tablet containing 5-aminosalicylic acid obtained in Example 4 was press-coated with hydroxypropylmethylcellulose (trade name: Metolose 60SH-400, available from The Shin-etsu Chemical Go., Ltd.) in a coating amount of 200 mg per tablet by means of a press-coating machine (Correct 18HUK-DC Type, made by Kikusui Seisakusho Ltd.) to obtain a press-coated tablet having a diameter of 9 mm and a weight of 270 mg.

Then, the obtained press-coated tablet was spray-coated with a 8 w/w % coating solution of hydroxypropylmethylcellulose phthalate (trade name: HPMCP, available from The Shin-etsu Chemical Co., Ltd.) dissolved in 80 w/w % ethanol, in a coating amount of 30 mg per tablet by means of a fluidized bed coating apparatus (MODEL HCT-MINI HICOATER, made by Freund Ind. Co., Ltd.) to obtain a pharmaceutical preparation of the present invention.

With respect to thus obtained pharmaceutical preparation of the present invention, a dissolution test was carried out with the second fluid of the test in JPXII under the same conditions in Example 1. In the second fluid, the medicinal active ingredient was quickly released after the lag-time of about 4 hours.

EXAMPLE 7

The plain tablet containing 5-aminosalicylic acid obtained in Example 4 was press-coated with hydroxypropylmethylcellulose (trade name: Metolose 60SH-400, available from The Shin-etsu Chemical Co., Ltd.) in a coating amount of 200 mg per tablet by means of a press-coating machine (Correct 18HUK-DC Type, made by Kikusui Seisakusho Ltd.) to obtain a press-coated tablet having a diameter of 9 mm and a weight of 270 mg.

Then, the obtained press-coated tablet was spray-coated with a 8 w/w % coating solution of hydroxypropylmethylcellulose acetate succinate (trade name: HPMCAS-M, available from The Shin-etsu Chemical Co., Ltd.) and triethyl citrate (the mixing ratio, 10:1) dissolved in 80 w/w % ethanol, in a coating amount of 30 mg per tablet by means of a fluidized bed coating apparatus (MODEL HCT-MINI HICOATER, made by Freund Ind. Co., Ltd.) to obtain a pharmaceutical preparation of the present invention.

With respect to thus obtained pharmaceutical preparation of the present invention, a dissolution test was carried out with the second fluid of the test in JPXII under the same conditions in Example 1. In the second fluid, the medicinal active ingredient was quickly released after the lag-time of about 4 hours.

Experimental Example 1

Figure 2:
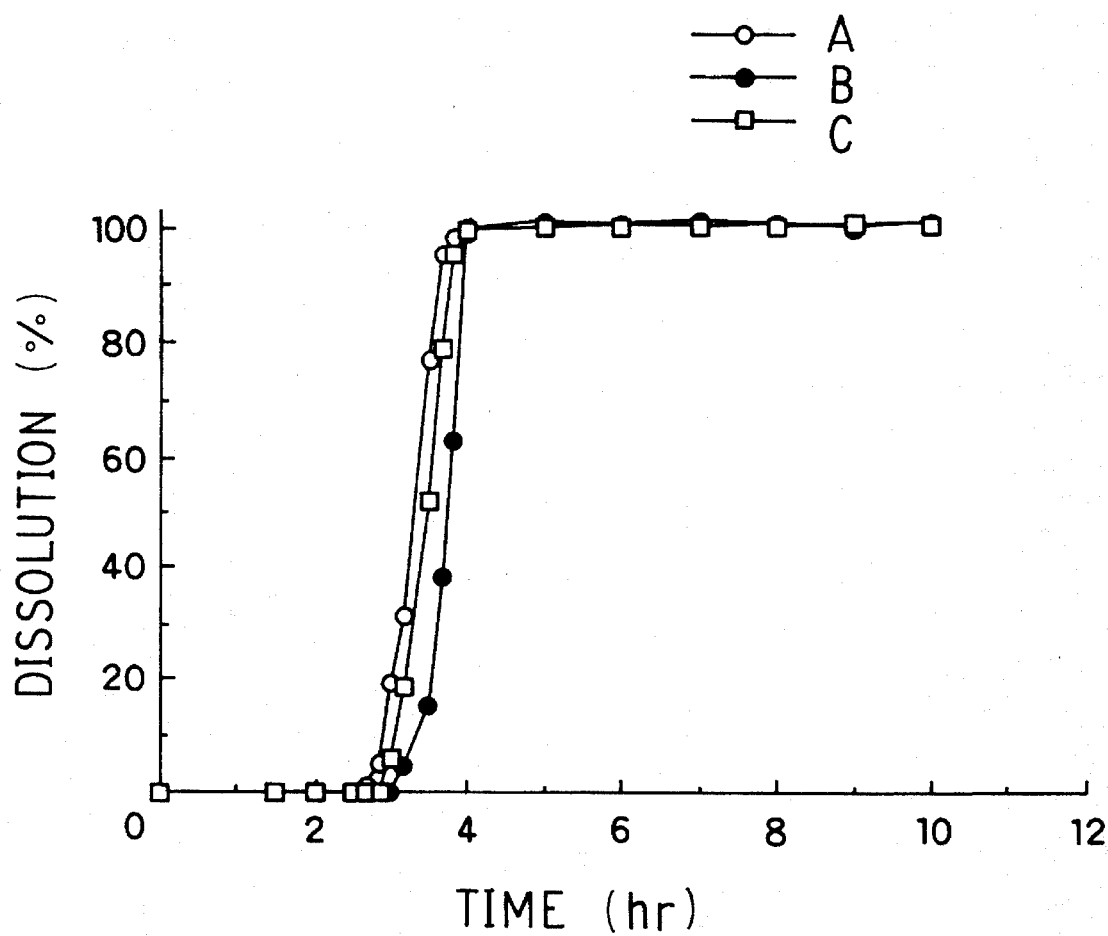
FIG. 2 is a graph showing the result of the dissolution test with the second fluid of the dissolution test in JPXII using a pharmaceutical preparation after immersing in the first fluid of the dissolution test in JPXII for a certain time in Experimental Example 1.

With respect to the pharmaceutical preparation obtained in Example 1, after immersing in the first fluid of the test in JPXII for a certain time, a dissolution test was carried out with the second fluid of the test in JPXII (the other conditions were the same as in Example 1). The results of the test are shown in FIG. 2. The dissolution patterns A, B and C represent the results of the dissolution test with the second fluid using the pharmaceutical preparations previously immersed in the first fluid for 0, 8 and 16 hours, respectively. As it is clear from the dissolution patterns of diltiazem hydrochloride, independent on the immersed time first fluid, each pharmaceutical preparation showed almost the same dissolution pattern of which the lag-time is about 3 hours in the second fluid.

The above-mentioned results suggest that when the pharmaceutical preparation of the present invention is orally administered, without being influenced by the variation of the length of the residence time of the pharmaceutical preparation the stomach, the eventual release of the medicinal active ingredient starts only at about 3 hours after reaching the small intestine.

Experimental Example 2

Figure 3:
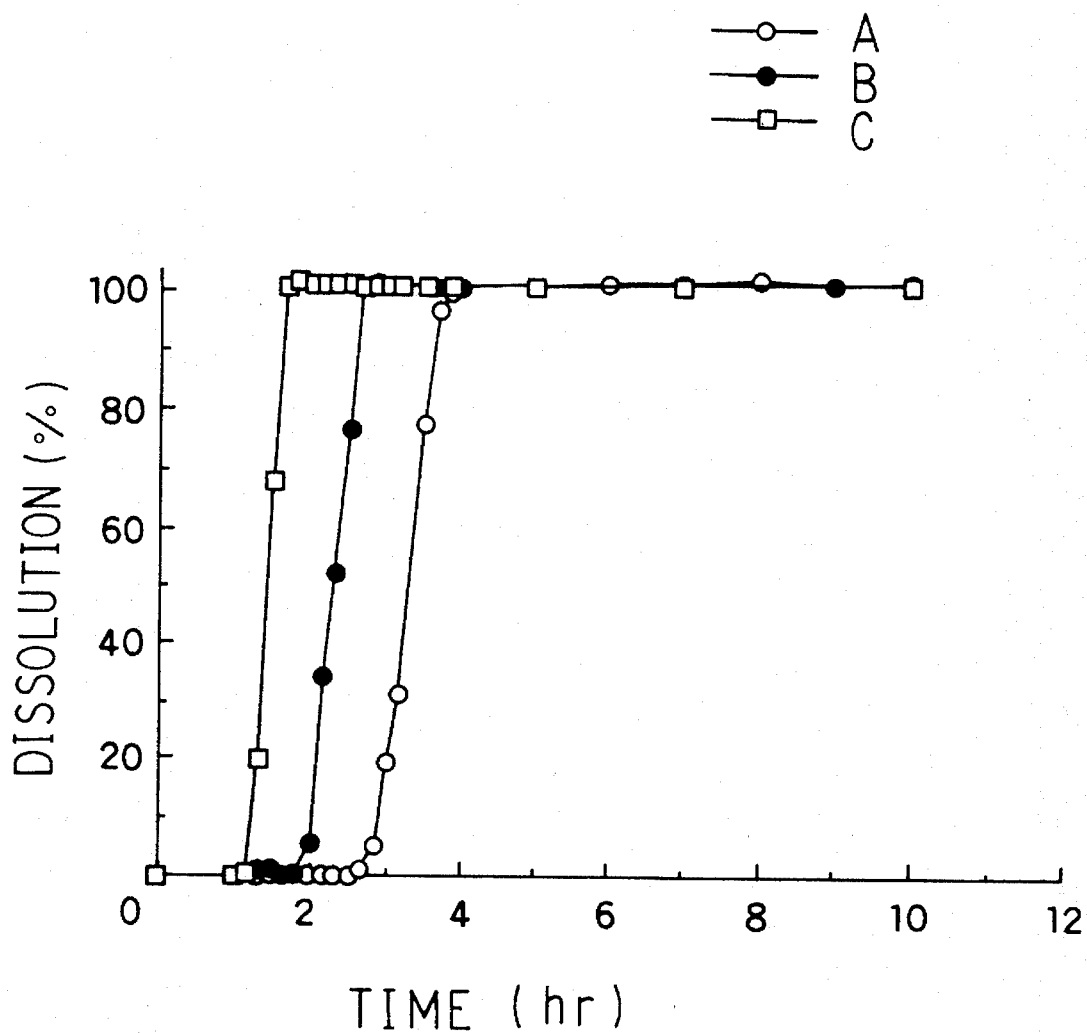
FIG. 3 is a graph showing the result of the dissolution test with the second fluid of the dissolution test in JPXII using three kinds of pharmaceutical preparations having different coating amounts of the press-coated layer in Experimental Example 2.

Three kinds of the pharmaceutical preparations of the present invention were prepared by the same way as in Example 1 except that the amount per tablet of the mixture of powder of hydroxypropylcellulose (trade name: HPC-L, having a viscosity of 6 to 10 cps as measured at 20° C. in a 2% aqueous solution, available from Nippon Soda Co., Ltd.) and hydroxypropylcellulose (trade name: HPC-M, having a viscosity of 150 to 400 cps as measured at 20° C. in a 2% aqueous solution, available from Nippon Soda Co., Ltd.) (the mixing ratio, 9:1) was changed to 200 mg, 160 mg and 140 mg, respectively. With respect to these pharmaceutical preparations, dissolution tests were carried out with the second fluid of the test in JPXII (the other conditions were the same as in Example 1). The results are shown in FIG. 3. The pharmaceutical preparations A, B and C represent the obtained pharmaceutical preparations wherein the amount of the press-coated layer per tablet is 200 mg, 160 mg and 140 mg, respectively. All pharmaceutical preparations A, B and C showed unique pulsatile dissolution patterns. The lag-times in each pharmaceutical preparation were about 3 hours, about 2 hours and about 1 hour, respectively. That is, the amount of the press-coated layer of these pharmaceutical preparations was lesser, the lag-time was shorter.

These results suggest that when these three kinds of the pharmaceutical preparations having different amounts of the press-coated layer are orally administered, the release of the medicinal active ingredient can start at a different site in the intestine, individually.

In addition to the ingredients used in the Examples, other ingredients can be used in the Examples as set forth in the specification to obtain substantially the same results.

What is claimed is:

1. A pharmaceutical preparation for oral administration comprising (a) a core containing a medicinal active ingredient, (b) a press-coated layer comprising hydroxypropylcellulose, said layer being provided around the core and (c) a film comprising an enteric polymer, said film being provided around the press-coated layer, wherein a coating amount of the film (c) is 5 to 50% by weight based on a total weight of the core (a) and the press-coated layer (b), and a coating amount of the press-coated layer (b) is 150 to 600% by weight based on a weight of the core (a).

2. The pharmaceutical preparation of claim 1, wherein said hydroxypropylcellulose is a mixture of two kinds of hydroxypropylcelluloses having a viscosity of 6 to 10 cps and a viscosity of 150 to 400 cps, respectively, as measured in a 2% aqueous solution at 20° C., in a mixing ratio of 9:1 to 1:9 by weight.

3. The pharmaceutical preparation of claim 1 or 2, wherein the enteric polymer is carboxymethylethylcellulose, hydroxypropylmethylcellulose phthalate, hydroxypropylmethylcellulose aceate succinate or poly(methyacrylic acid, methyl methacrylate).

4. The pharmaceutical preparation of claim 1, wherein the press-coated layer (b) is capable of suppressing release of a medicinal active ingredient until the pharmaceutical preparation reaches near a targeted site in the intestinal tract, and the film (c) is capable of preventing penetration of water into the pharmaceutical preparation during residence in the stomach.

* * * * *